(12) United States Patent
Firouzian et al.

(10) Patent No.: US 9,710,915 B2
(45) Date of Patent: Jul. 18, 2017

(54) AUTOMATIC BACKGROUND REGION SELECTION FOR LESION DELINEATION IN MEDICAL IMAGES

(71) Applicant: Siemens Medical Solutions USA, Inc., Malvern, PA (US)

(72) Inventors: Azadeh Firouzian, Oxford (GB); Jens Kaftan, Oxford (GB); Matthew David Kelly, Botley (GB); Antonios Makropoulos, Enysham (GB)

(73) Assignee: Siemens Medical Solution USA, Inc., Malvern, PA (US)

( * ) Notice: Subject to any disclaimer, the term of this patent is extended or adjusted under 35 U.S.C. 154(b) by 0 days.

(21) Appl. No.: 14/796,361

(22) Filed: Jul. 10, 2015

(65) Prior Publication Data

US 2016/0012604 A1 Jan. 14, 2016

(30) Foreign Application Priority Data

Jul. 11, 2014 (GB) .................................. 1412394.7

(51) Int. Cl.
| | |
|---|---|
| *G06K 9/00* | (2006.01) |
| *G06T 7/00* | (2017.01) |
| *G06F 17/30* | (2006.01) |
| *A61B 6/03* | (2006.01) |
| *A61B 6/12* | (2006.01) |
| *A61B 6/00* | (2006.01) |
| *G06T 7/11* | (2017.01) |
| *G06T 7/194* | (2017.01) |
| *G06T 7/136* | (2017.01) |

(Continued)

(52) U.S. Cl.
CPC ............ *G06T 7/0081* (2013.01); *A61B 6/032* (2013.01); *A61B 6/037* (2013.01); *A61B 6/12* (2013.01); *A61B 6/5217* (2013.01); *A61B 6/5247* (2013.01); *G06F 17/30244* (2013.01); *G06T 7/11* (2017.01); *G06T 7/136* (2017.01); *G06T 7/194* (2017.01); *A61B 5/055* (2013.01); *A61B 5/7425* (2013.01); *G06T 2207/10081* (2013.01); *G06T 2207/10104* (2013.01); *G06T 2207/30096* (2013.01)

(58) Field of Classification Search
CPC .................................................... G06T 7/0081
See application file for complete search history.

(56) References Cited

U.S. PATENT DOCUMENTS

| | | |
|---|---|---|
| 5,825,910 A | 10/1998 | Vafai |
| 2006/0079743 A1* | 4/2006 | Ferrant .................. A61B 6/032 |
| | | 600/407 |

(Continued)

OTHER PUBLICATIONS

Conson et al (NPL: "Automated delination of Brain Structure in Patient undergoing radiotherapy for primary brain tumors: From Atlas to dose-volume histograms", Radiotherapy and Oncology, Elsevier 0167-8140/ 2014 Elsevier Ireland Ltd.).*

(Continued)

*Primary Examiner* — Oneal R Mistry
(74) *Attorney, Agent, or Firm* — Schiff Hardin LLP

(57) ABSTRACT

In a method and apparatus for automatic background region selection for lesion segmentation in medical images, a patient medical image dataset is loaded into a computer and an image region is delineated to obtain a segmentation containing a lesion. A background region is created from the segmentation representing the patient organ.

9 Claims, 4 Drawing Sheets

(51) Int. Cl.
*A61B 5/00* (2006.01)
*A61B 5/055* (2006.01)

(56) References Cited

U.S. PATENT DOCUMENTS

| | | | |
|---|---|---|---|
| 2007/0053491 A1* | 3/2007 | Schildkraut | A61N 5/1049 378/65 |
| 2007/0081710 A1 | 4/2007 | Hong et al. | |
| 2008/0002873 A1 | 1/2008 | Reeves et al. | |
| 2008/0069414 A1* | 3/2008 | Manjeshwar | G06K 9/00 382/128 |
| 2008/0260221 A1 | 10/2008 | Unal et al. | |
| 2008/0273784 A1* | 11/2008 | Pfister | G06T 5/50 382/131 |
| 2009/0097728 A1 | 4/2009 | Lee et al. | |
| 2009/0129673 A1 | 5/2009 | Simon et al. | |
| 2009/0226060 A1* | 9/2009 | Gering | G06T 7/0081 382/128 |
| 2010/0238170 A1* | 9/2010 | Ekin | G06T 7/0012 345/424 |
| 2012/0087561 A1* | 4/2012 | Guetter | G06T 7/0083 382/131 |
| 2012/0123253 A1* | 5/2012 | Renisch | A61B 6/5217 600/425 |
| 2012/0219200 A1 | 8/2012 | Reeves et al. | |
| 2013/0267830 A1* | 10/2013 | Ojha | A61B 5/055 600/411 |
| 2014/0029832 A1 | 1/2014 | Molnar et al. | |
| 2014/0304271 A1 | 10/2014 | Lu et al. | |
| 2015/0042646 A1* | 2/2015 | Comaniciu | G06T 17/20 345/420 |
| 2015/0055849 A1* | 2/2015 | Galavis | G06T 7/0012 382/132 |
| 2015/0112197 A1* | 4/2015 | Bharat | A61N 5/1049 600/438 |
| 2015/0119689 A1* | 4/2015 | Pascual-Leone | A61N 2/006 600/410 |

OTHER PUBLICATIONS

Schaefer et al. "A Contrast-Orientated Algorithm for FDG-PET-based Delineation of Tumour Volumes for the Radiotherapy of Lung Cancer" European Journal of Nuclear Medical Molecular Imaging; vol. 35, pp. 1989-1999 (2008).

Boellaard et al., "Effects of Noise, Image Resolution and ROI Definition on the Accuracy of Standard Uptake Values: A Simulation Study," Sound of Nuclear Medicine, vol. 45, No. 9, pp. 1519-1527 (2004).

* cited by examiner

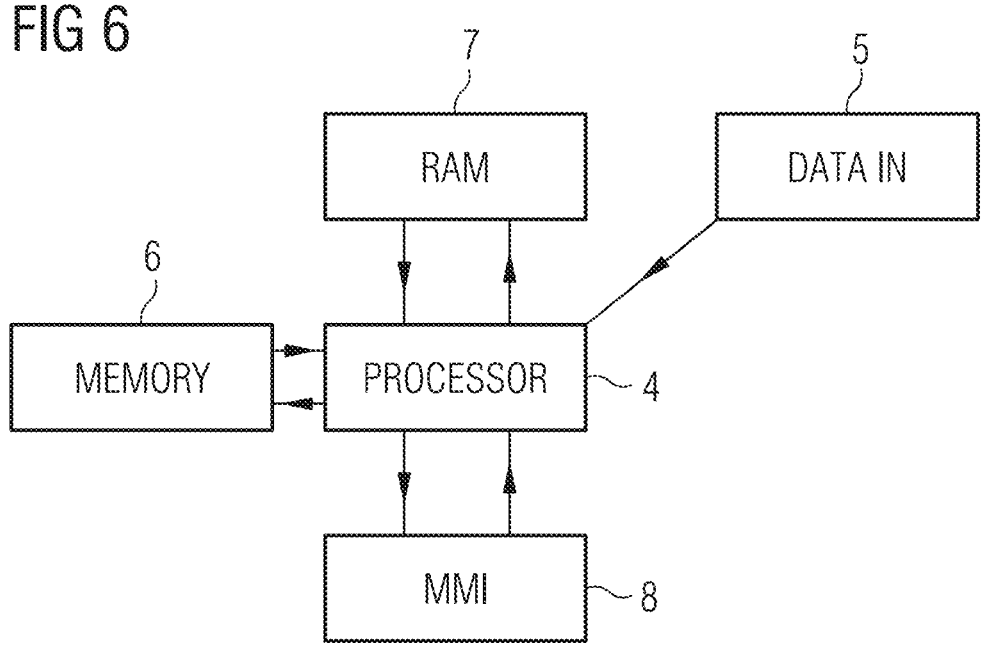

AUTOMATIC BACKGROUND REGION SELECTION FOR LESION DELINEATION IN MEDICAL IMAGES

BACKGROUND OF THE INVENTION

Field of the Invention

The present invention concerns a method and apparatus for automatically identifying a background region in order to facilitate delineation in a medical image of lesion.

Description of the Prior Art

When treating cancer using radiation or monitoring a tumor's response to the treatment, definition of gross tumor volume (GTV) is critical. GTV can be distinguished using anatomical imaging techniques such as CT or MRI. Functional imaging techniques such as PET or SPECT, on the other hand, can provide additional insight on the structure of the tumor and its metabolic activity which is used extensively as well in the treatment process. Metabolic activity may be expressed in terms of metabolic tumor volume or MTV.

Accurate shape and volume determination of lesions will help clinicians to reduce radiation damage to healthy tissues surrounding the lesion and deliver maximum radiation dose to the tumor. Accurate shape and volume determination of lesions will also help clinicians assess changes in metabolic volume in response to therapy more accurately. Therefore numerous studies have been performed on developing automated methods for tumor delineation. These delineation methods differ in terms of methodology but they often need an initialization which gives the algorithm some information about the lesion region and its background. Such initial information must to be provided by a user.

In a typical patient medical image, a lesion area is visible in the image, but the background area is prone to being defined very subjectively and therefore inconsistently. A lesion area would typically be visible, but the boundary with the background is typically not clear due to the resolution of the image, and image noise. These factors contribute to the variability in manual delineation. Furthermore, due to the complex shape of many background regions and the requirement to exclude non-background regions, the background area is time-consuming to create. In addition, the lesion delineation results produced by some algorithms may vary significantly depending on the initial background region definition. Such variation may affect the treatment planning substantially. Consistency in the background region is therefore needed. The present invention provides a solution for automated selection of the background region for automated lesion delineation.

Currently, the background region for automated lesion delineation is typically defined manually by the user by placing an ROI (region of interest) in a healthy region of an organ containing a lesion. This step makes the definition procedure user-dependent and time consuming for clinicians. Automatic delineation methods have the advantage of being less user-dependent, and methods that consider background uptake are typically more accurate than those that do not. However, the requirement to define a background region creates additional work for the clinician and introduces more subjectivity.

The ROI is typically a sphere or a rectangle because such shapes are easy to define with quick mouse interactions or similar. Other ROIs may have more complex shapes if certain regions of the image need to be avoided: for example, in the case of a lung lesion close to the diaphragm, the background region should include the lung but not the mediastinum or GI tract: this may not be possible with simple ROI spheres or rectangles, and therefore more complex shapes should be used, which is even more time consuming for the clinician.

Background prior art, which may assist in the understanding of the present invention, includes:

A. Schaefer, S. Kremp, D. Hellwig, C. Rübe, C.-M. Kirsch, and U. Nestle, "*A contrast-oriented algorithm for FDG-PET-based delineation of tumor volumes for the radiotherapy of lung cancer: derivation from phantom measurements and validation in patient data.,*" Eur. J. Nucl. Med. Mol. Imaging, vol. 35, no. 11, pp. 1989-99, Nov. 2008.

R. Boellaard, N. C. Krak, O. S. Hoekstra, and A. a Lammertsma, "*Effects of noise, image resolution, and ROI definition on the accuracy of standard uptake values: a simulation study.,*" J. Nucl. Med., vol. 45, no. 9, pp. 1519-27, Sep. 2004.

SUMMARY OF THE INVENTION

An object of the invention is to provide a method for automatically creating a background region for a selected lesion by integrating two image analysis methodologies.

The above object is achieved in accordance with the present invention by a method and an apparatus for automatic background region selection for region segmentation in medical image data, wherein a medical image data set of a patient is loaded into a processor and, in the processor, an algorithm is automatically executed in order to delineate an image region in the medical image data that is a segmentation of a region within the medical image data that contains a lesion. From this segmentation, an automatic identification takes place in the processor of a background region, and the segmentation of the lesion is then calculated by comparison with the background region within the segmentation of the region that contains the lesion.

BRIEF DESCRIPTION OF THE DRAWINGS

FIG. 6 schematically shows an apparatus according to an embodiment of the invention.

DESCRIPTION OF THE PREFERRED EMBODIMENTS

Certain embodiments of the present invention use an automated organ delineation tool which delineates an image region representing a patient organ. In an example, a co-registered PET (functional) and CT (anatomical) dataset may be used. In other examples, a single functional image data set may be used.

For a given target lesion, the background region is created from a delineation of an organ containing the lesion, by excluding all regions that are assumed not to be part of the background region. These regions include all representations of lesions and similar representations in terms of intensity values and shape in the organ of interest. For example, this may be defined as hotspots within a set of pre-determined SUV (standardized uptake value) thresholds in the PET image data.

In an exemplary embodiment, lung vessels or other lesions are taken to have an increased level of uptake relative to the background, as with the lesion of interest, and so can be removed from the background, for example by excluding regions above a certain threshold which could be defined a priori, or which could be estimated from the ROI itself using a histogram analysis.

Another example could be liver lesions. In the liver, areas of low intensity may be indicative of a lesion and the background should include only ROIs that show typically expected level of uptake represented by an intensity value in the image. Therefore, the background region may exclude regions below a certain threshold.

Figure 1:
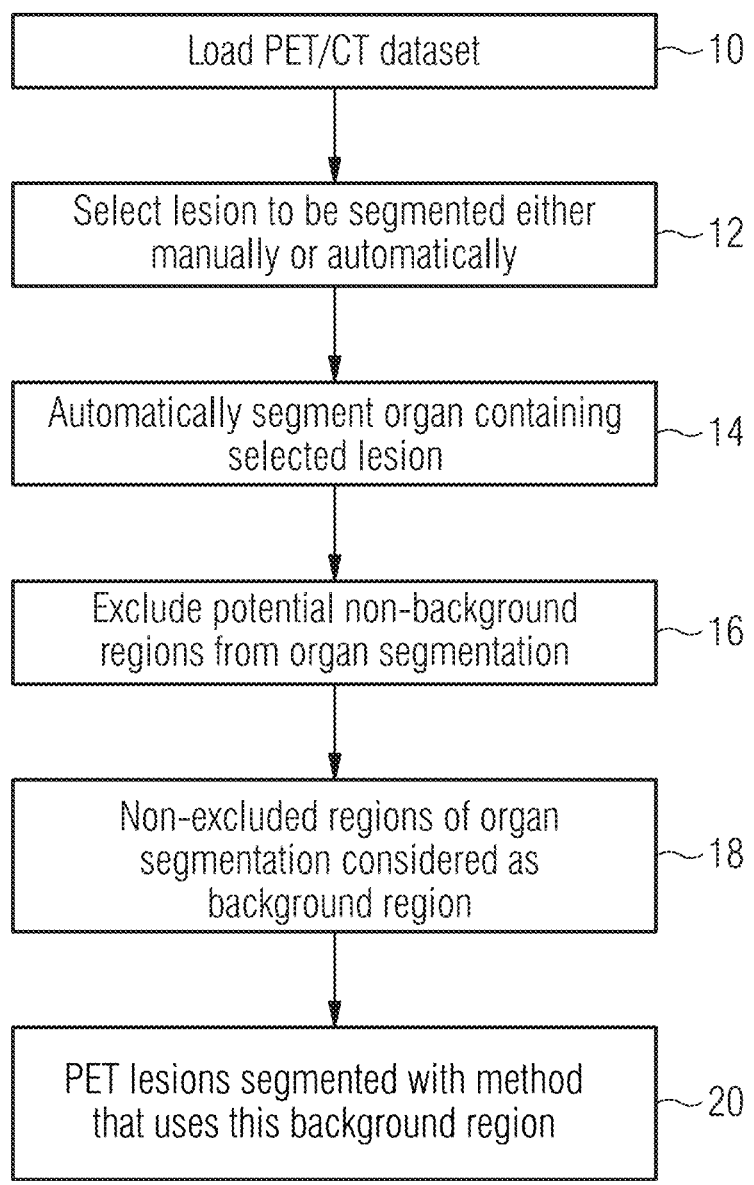
FIG. 1 is a flowchart illustrating steps in a method according to the present invention, applied to an example patient dataset with a lung lesion.

In FIG. 1, the steps of an exemplary embodiment of the present invention relating to a lung lesion case on a PET/CT image are shown.

At step 10, a patient medical image dataset is loaded. In this example, and typically, it is a combined functional and anatomical image data set, captured in multiple modalities—here, PET and CT.

Figure 2:
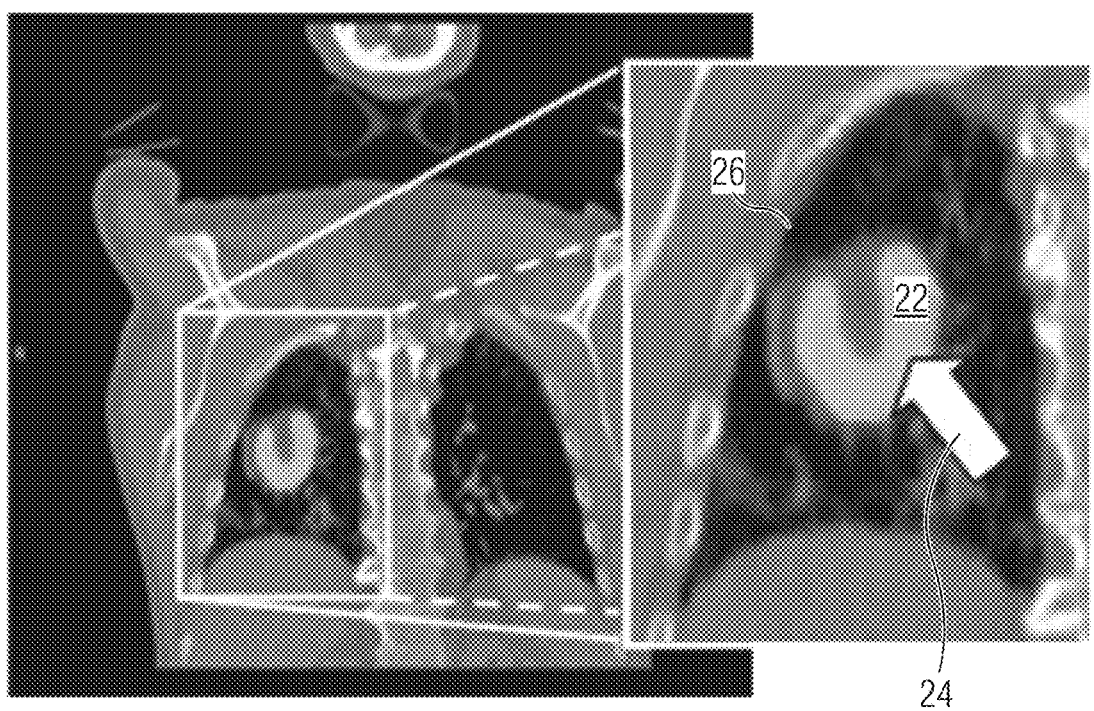
FIGS. 2-5 show examples of image data for the purpose of explaining the present invention. In each case, part of a patient medical image data set is shown, relating to the upper torso, with an enlarged part showing the image region of the right lung—the organ of interest in the present example. The illustrations shown in FIGS. 2-5 are provided for explanation only, and do not represent a complete embodiment of the present invention.

At step 12, a lesion to be segmented is selected, in this example in the PET, or functional, image. In FIG. 2, this is represented by arrow 24 indicating representation 22 of a lesion within lung 26. In an embodiment of the invention, arrow 24 may be a cursor on a display screen showing the patient medical image data, and selection of the lesion may be achieved by pointing the cursor (arrow 24) to the representation of the lesion and selecting it by a mouse click or keyboard entry, or similar.

Figure 3:
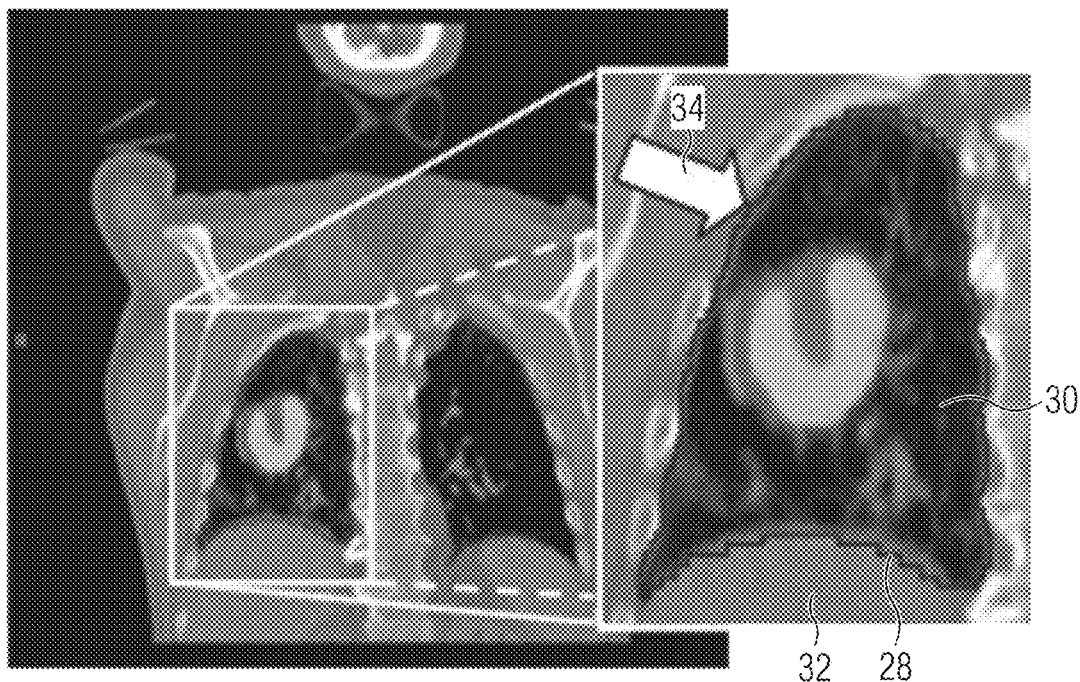

In step 14, represented in FIG. 3, this exemplary embodiment of the invention reacts by calculating an organ segmentation 28, representing the boundary of the organ containing the lesion selected in step 12. This may be done using the co-registered CT, or anatomical, image to identify a closed region 30 around the representation of the lesion 22, that corresponds to the organ 28 (e.g., lung), or body region (e.g., abdomen) containing the lesion. This segmentation method may use a combination of voxel intensities and shape priors to identify the boundary 28 of that region 30 where it meets a next region 32 corresponding to a different organ or body region. The segmentation 28 is illustrated by a line in FIG. 3, pointed out by arrow 34. Once created, this CT, anatomical image-derived organ segmentation 28 can be transferred to the co-registered PET, functional, image: for example, by interpolation of the segmentation mask.

Figure 4:
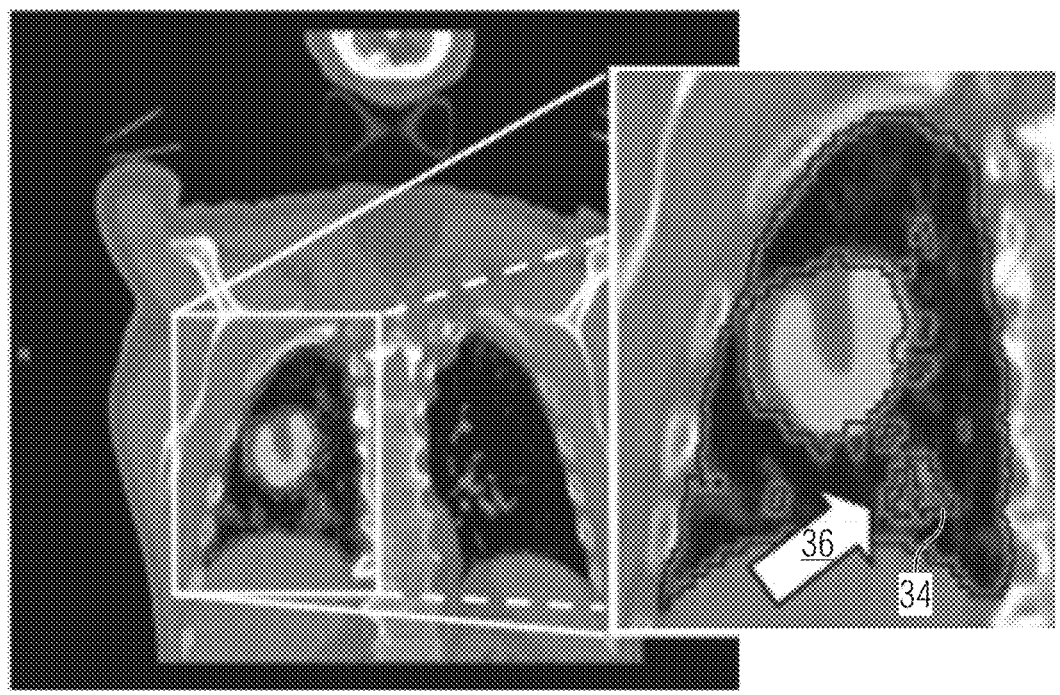

In step 16, illustrated in FIG. 4, potential non-background regions are identified, from within the organ segmentation, following transfer to the PET, or functional, image. This may be achieved by setting a threshold intensity value on the PET, or functional, image data and identifying all regions within the segmentation 28 that have an intensity value above a certain threshold. The intensity value may be defined in terms of SUV. The threshold value should be lower than the intensity shown by the representation of the lesion 22 but higher than the average intensity of the organ segmentation other than the representation of the lesion 22. Potential non-background regions 34 may also be filtered so that regions that are shaped unlike lesions, either in the functional or anatomical image, perhaps by virtue of their aspect ratio in two- or three-dimensions, may be excluded. Such identified potential non-background regions 34 are shown outlined in FIG. 4 and indicated by arrow 36. The illustrated outlines may be calculated by a processor in a computer implemented embodiment of the present invention, and shown on an associated display screen.

At step 18, those remaining regions of segmentation 28 on the PET image, that is, those regions that have not been identified as potential non-background regions, are considered to be background regions. This information may be used in further processing of the image data.

In an alternative embodiment of the invention, the background region may be determined using the PET, or functional, data alone. For example, a region growing method may be used to identify a set of connected voxels in the neighborhood of the lesion that excludes local maxima, which may represent non-background regions. This set of connected voxels is then deemed to be the background region.

The data from the background region are used to generate the lesion segmentation. For example, lesion segmentation may be carried out by computing a mean intensity in the background region in the PET image, then taking a percentage of the difference between this mean background value and the maximum value in the lesion as the threshold for lesion segmentation.

Figure 5:
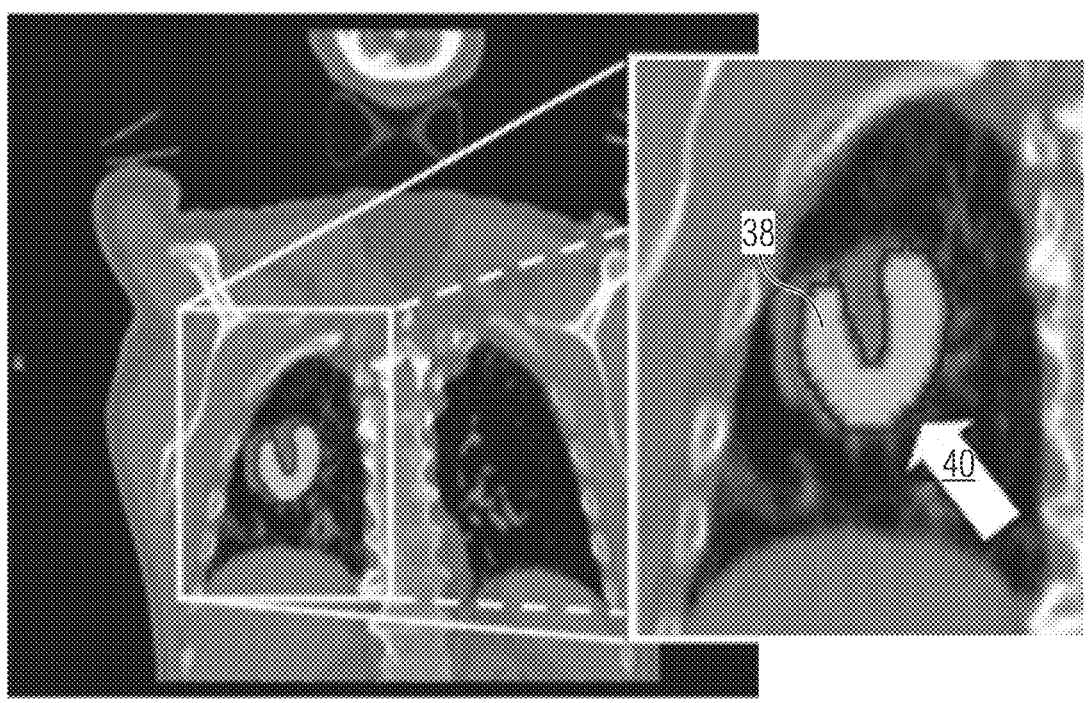

Finally, at step 20 and as illustrated in FIG. 5, lesions 38 are segmented in the PET image data. The background regions identified in earlier steps may be used to establish criteria for lesion segmentation, such as discussed in the preceding paragraph. Thresholding of SUV intensity may be applied to the remaining image data, described as potential non-background regions above to identify segmentation 38 of a lesion in the PET image data set. The resultant segmentation 38 is shown by arrow 40 in FIG. 5.

As a result, the lesion may be consistently, rapidly and automatically identified with accuracy, allowing its volume to be calculated correctly, while reducing the amount of calculation required, due to the exclusion of the calculated background region from some steps of the calculation.

Alternative methods for identifying potential non-background regions include SUV thresholding in the PET image data; or a CAD-based method such as CT Lung CAD.

The size of the background region considered may be adjusted, for example where the lesion delineation method does not need a large background region.

The potential non-background regions could be dilated prior to exclusion by varying amounts to account for spill out in the PET image that may affect quantification of the background.

While the invention has been described with respect to multimodal image data captured in PET and CT, the method could be applied to other combinations of imaging modalities, such as PET/MR, SPECT/CT. As described above, a variant of the present invention may be applied to single-mode image data such as captured in a single functional modality such as PET.

The method and apparatus according to the present invention can be used for extensive statistical analysis of different image structures, for example derivation of background region distribution pattern.

In a further embodiment of the invention, the method could be extended to consider background regions that do not consist of a single, whole organ for example, the background region may represent individual lobes of the lung, contralateral head and neck region, or multiple abdominal organs.

In certain embodiments, the patient medical image dataset includes representations of a plurality of lesions. The method of the invention then comprises selecting a lesion of interest prior to the delineating step.

Referring to FIG. 6, the above embodiments of the invention may be conveniently realized as a computer system suitably programmed with instructions for carrying out the steps of the methods according to the invention.

For example, a central processing unit 4 is able to receive data representative of medical image data via a port 5 which could be a reader for portable data storage media (e.g. CD-ROM); a direct link with apparatus such as a medical scanner (not shown) or a connection to a network.

For example, in an embodiment, the processor performs such steps as loading a patient medical image dataset; delineating an image region to obtain a segmentation containing a lesion; creating a background region from the segmentation representing the patient organ by automatically identifying regions of the segmentation as lesions and potential non-background regions, and automatically identifying a background region by subtracting from the segmentation, the regions of the segmentation identified as lesions and potential non-background regions.

Software applications loaded on memory 6 are executed to process the image data in random access memory 7.

A Man—Machine interface 8 typically includes a keyboard/mouse/screen combination which allows user input such as initiation of applications and a screen on which the results of executing the applications are displayed.

Certain embodiments of the present invention accordingly provide a system and method to automatically generate a background region for lesion delineation methods on functional images. The organ or body region containing the selected lesion is automatically delineated from a registered anatomical image. Potential non-background regions are identified based on voxel intensity in the functional image and excluded.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatic segmentation of a depiction of a lesion in a functional medical image data set, comprising:
    loading a medical image data set into a computer, said medical image data set comprising a functional medical image data set and an anatomical image data set, both obtained from a patient but with respectively different imaging modalities, said functional medical image data set and said anatomical image data set being in registration with each other in said medical image data set;
    in said computer, automatically identifying and delineating an image region in said anatomical image data set that contains a lesion;
    in said computer, using the registration of said functional image data set and said anatomical image data set to apply the delineation of said image region identified in said anatomical image data set in order to delineate said image region also in said functional medical image data set;
    in said computer, within the delineated image region in said functional medical image data set, automatically identifying a potential lesion region surrounding a depiction of said lesion in said functional medical image data set, and potential non-background regions depicted in said functional medical image data set;
    in said computer, automatically identifying a background region in said delineated image region in said functional medical image data set, by subtracting said potential lesion region and said potential non-background regions from the functional medical image data set within said delineated image region;
    in said computer, segmenting said lesion in said functional medical image data set by differentiating the depiction of the lesion in said functional medical image data set from said background region; and
    at a display in communication with said computer, depicting the segmented lesion in a display of said functional image data set.

2. A method as claimed in claim 1 comprising selecting said functional medical image data set from the group consisting of a positron emission tomography (PET) data set and a single photon emission computed tomography (SPECT) data set, and selecting said anatomical image data set from the group consisting of a computed tomography (CT) data set and a magnetic resonance (MR) data set.

3. A method as claimed in claim 1 comprising segmenting said lesion in said functional medical image data set using a threshold by computing a mean intensity in said background region, determining a percentage of a difference between said mean intensity in said background region and a maximum intensity value in said lesion as said threshold, and using said threshold to perform segmentation of said lesion.

4. A method as claimed in claim 1 comprising identifying and delineating said image region in said anatomical image data set that contains said lesion by identifying and delineating an organ of the patient that contains said lesion.

5. A method as claimed in claim 4 comprising delineating said image region in said anatomical image data set by executing an automated organ delineating algorithm.

6. A method as claimed in claim 1 comprising identifying regions, in said image region delineated in said functional medical image data set, having an intensity value above a predetermined threshold as said potential non-background regions.

7. A method as claimed in claim 1 comprising, in said image region delineated in said functional medical image data set, identifying regions having an intensity value below a predetermined threshold as said potential non-background regions.

8. A method as claimed in claim 1 wherein said medical image data set contains multiple lesions, and selecting a lesion of interest, among said multiple lesions, before identifying and delineating said image region in said anatomical image data set.

9. A method as claimed in claim 1 comprising identifying said potential non-background regions, in said image region delineated in said functional medical image data set, by filtering according to an aspect ratio of respective shapes of said potential non-background regions, in two dimensions or three dimensions.

* * * * *